United States Patent [19]

Ishihara

[11] Patent Number: 4,958,768

[45] Date of Patent: Sep. 25, 1990

[54] ARTIFICIAL POTTED FLOWER

[76] Inventor: Yoshiko Ishihara, 8-7, Mori Minami 1-chome, Higashinadaku, Kobe, Japan

[21] Appl. No.: 274,237

[22] Filed: Nov. 21, 1988

[51] Int. Cl.$^5$ .......................... A61L 9/04; A01N 25/04
[52] U.S. Cl. ..................... 239/34; 424/76.3; 239/211
[58] Field of Search .............. 47/44, 41.12, 41 R, 47/41 SS, 39, 48.5; D23/366, 367; 424/76.4, 456, 487, 76.3, 76.1; 239/34, 54, 60; 428/35.5, 905

[56] References Cited

U.S. PATENT DOCUMENTS

| | | | |
|---|---|---|---|
| 3,016,199 | 1/1962 | Keydel | 47/41.12 X |
| 3,596,833 | 8/1971 | Gould | 239/54 |
| 3,804,331 | 4/1974 | Levey | 47/48.5 X |
| 4,540,721 | 9/1985 | Staller | 239/54 X |
| 4,748,069 | 5/1988 | Cullen | 206/204 X |
| 4,780,370 | 10/1988 | Pointier | 428/905 X |
| 4,860,953 | 8/1989 | Hsien | 239/211 X |

FOREIGN PATENT DOCUMENTS

| | | | |
|---|---|---|---|
| 59-57658 | 4/1984 | Japan | 424/76.4 |
| 551784 | 3/1943 | United Kingdom | 206/0.5 |

Primary Examiner—Danton D. DeMille
Attorney, Agent, or Firm—Jordan and Hamburg

[57] ABSTRACT

An artificial potted flower having a deodorant and/or scenting effect comprises an artificial flower, a vessel in which the artificial flower is planted, a pack consisting of a casing of soluble film and, contained therein, a mixture of a powdery deodorant and/or perfume and a powdery water-absorbent synthetic resin, the pack mentioned above being disposed within the vessel, a cover plate of porous synthetic resin fitted in a top portion of the vessel, and a support means for supporting the artificial flower the support means being disposed in the bottom portion of the vessel in such a manner that a stalk portion of the artificial flower may be passed through the cover plate and secured rigidly to the support means. The artificial potted flower is highly ornamental, easy to transport and handle, and very easy to use, features a long duration of scenting and/or deodorant effect, and can be installed in very stable position.

3 Claims, 6 Drawing Sheets

ARTIFICIAL POTTED FLOWER

BACKGROUND OF THE INVENTION a. Technical Field of the Invention

This invention relates to an artificial potted flower which assures a prolonged deodorant and/or scenting effect.

b. Prior Art

The hithereto-known artificial potted flower is so constructed that a liquid perfume contained in a vessel, typically a pot, is sucked up by capillary action via the stalk portion of an artificial flower into its petals and leaves and released from the petals and leaves into the ambient atmosphere. Though such an artificial flowerpot assembly assures an almost immediate scenting effect, the consumption of the liquid perfume is so rapid that the desired scent may last only a brief time period. Moreover, upon exhaustion of the liquid perfume, it must be replenished at a short interval and hence a stock of liquid perfume must be maintained on hand.

On the other hand, there has not been available an artificial potted flower designed to eliminate malodors such as the smell of cigaret smoke.

OBJECT OF THE INVENTION

Having been accomplished under the above circumstances, this invention has as its object to provide an artificial potted flower which assures a prolonged deodorant and/or scenting effect and is pleasing enough to the eye to serve an ornamental function.

SUMMARY OF THE INVENTION

To accomplish the above object, this invention is directed to an artificial potted flower comprising an artificial flower, a vessel in which the artificial flower is planted, a pack consisting of a casing of soluble film and, contained therein, a mixture of powdery deodorant and/or perfume and powdery water-absorbent synthetic resin, the pack being disposed within the vessel, a cover plate of porous synthetic resin as fitted in a top portion of the vessel, and a support means for supporting the artificial flower the support means being disposed in the bottom portion of the vessel in such a manner that a stalk portion of the artificial flower may be passed through the cover plate and secured rigidly to the support means.

In the above arrangement, when water is poured over the cover plate made of porous synthetic resin, the water finds its way through the cover plate to reach the pack within the vessel, whereupon the soluble film casing of the pack is dissolved by the water. Thereupon, the water-absorbent synthetic resin in the pack absorbs water and swells to fill the free space in the vessel. As a result of the absorption of water by the water-absorbent synthetic resin, the deodorant and/or perfume contained in the pack is entrapped in the swollen gels of the water-absorbent synthetic resin and maintained securely in situ. The deodorant and/or perfume thus entrapped in the resin gels is released, by the moisture-releasing property of the water-absorbent resin in the case of a deodorant or by inherent sublimability in the case of a perfume, from the gels gradually into the ambient atmosphere through the porous cover plate of synthetic resin, thus assuring a prolonged deodorant and-/or scenting effect.

Because the artificial potted flower according to this invention incorporates powdery synthetic resin and powdery deodorant and/or powdery perfume, the overall weight of the product is reduced so that it can be conveniently transported or carried about. Moreover, by a simple procedure of pouring water over it, the deodorant and/or scenting effect can be assured for a sustained time period. Moreover, if the water lost by evaporation is made up for in use, the deodorant and/or perfume remaining in the water-absorbent synthetic resin is further emanated so that the duration of the deodorant and/or scenting effect can be further increased.

Furthermore, because the stalk portion of the artificial flower is supported by the cover plate fitted in the top portion of the vessel and its free end is rigidly secured in position by the support means located in the bottom of the vessel, the artificial flower can be accurately planted in the vessel and held with utmost stability in the vessel. Moreover, since the weight of the vessel is increased by the equivalent of the weight of water absorbed into the powdery water-absorbent synthetic resin, the stability of the entire artificial flowerpot assembly is further increased so that it does not easily fall down. Should it ever fall, the water-absorbent synthetic resin would not easily release the trapped water so that there is no fear of water issuing out from the vessel.

BRIEF DESCRIPTION OF THE DRAWINGS

More particularly, FIG. 1 is a partially exploded perspective view showing an artificial potted flower;

FIG. 2 is a disassembled view of the same artificial potted flower;

FIG. 3 is a partially exploded perspective view showing the pack;

FIG. 4 is a partially exploded perspective view showing the artificial potted flower after addition of water; and FIGS. 5 and 6 show another embodiment of this invention, wherein FIG. 5 is a cross-section view showing the artificial potted flower and FIG. 6 is a cross-section view showing the artificial potted flower after addition of water.

DETAILED DESCRIPTION OF PREFERRED EMBODIMENTS

Figure 1:
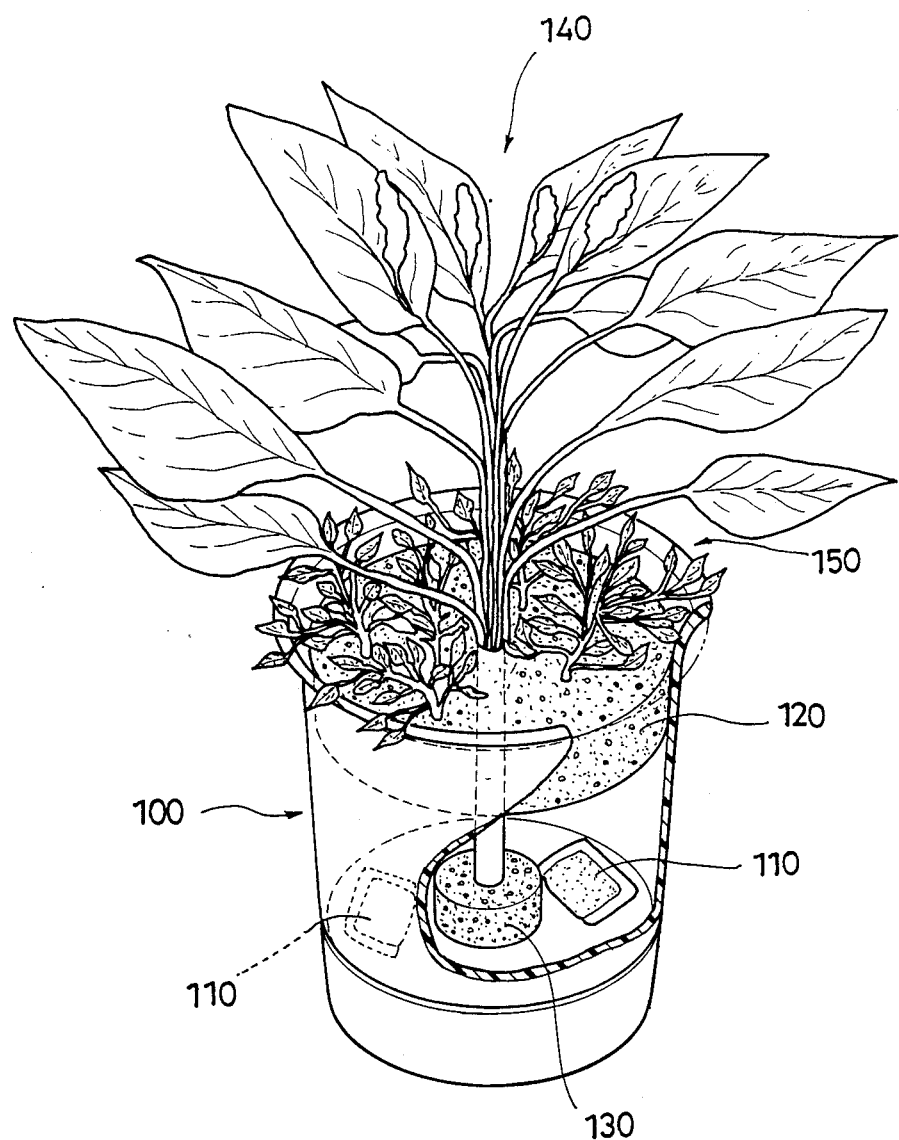
FIGS. 1 through 6 show artificial potted flowers embodying the principle of this invention.
Figure 2:
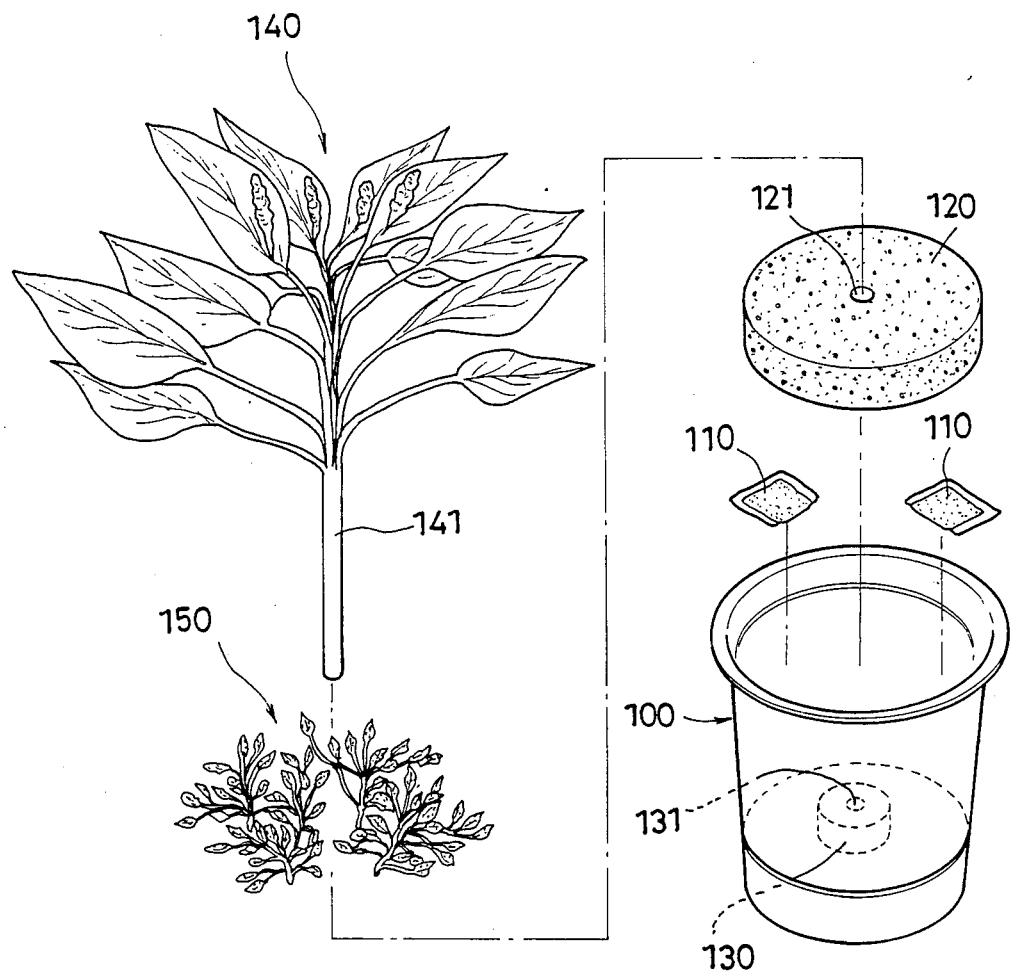

FIG. 1 is a partially exploded perspective view showing the artificial potted flower of this invention and FIG. 2 is a disassembled view of the same artificial potted flower. Disposed in a synthetic resin vessel 100 having a capacity of about 500 cc are two packs 110. Fitted in a top portion of said vessel 100 is a disk-shaped cover plate 120 made of a porous synthetic resin such as polyurethane foam and the cover plate 120 is formed with a central bearing hole 121. Rigidly mounted on the inner bottom of said vessel 100 is a small disk-shaped support means 130 made of polystyrene foam and this support means is centrally provided with a bearing hole 131.

In the vessel 100 provided as above with the packs 110, cover plate 120 and support means 130, an artificial flower 140 based on synthetic resin is planted by passing its stalk portion 141 into the bearing hole 121 of the cover plate 120 and bonding the same to the inner surface of the bearing hole 121 while inserting the bottom end of the stalk portion 141 into the bearing hole 131 of the support means 130. In addition, for an enhanced decorative effect of the artificial potted flower, a cluster of small artificial grass 150 is either bonded to or otherwise secured to the cover plate 120 to hide the latter.

Figure 3:
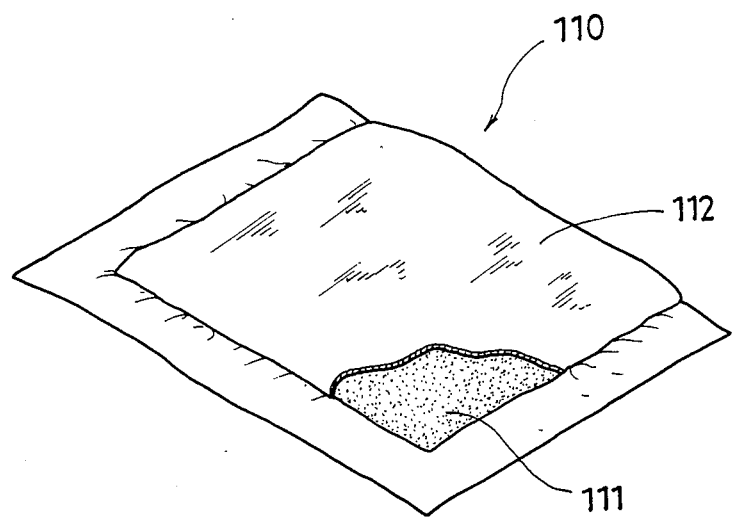

FIG. 3 is a partially exploded perspective view of the pack 110. Each of said packs 110 comprises a mixture 111 of 3 g of a powdery water-absorbent synthetic resin, i.e. a polyacrylic acid resin, 2 g of a powdery porous deodorant such as coral which is capable of adsorbing malodors and 2 g of a powdery perfume which is a perfume adsorbed on a porous substrate such coral as encased in a soluble film 112, i.e. a film of polyvinyl acetate, which is about 20 microns in thickness. When the above pack 110 is immersed in water, the soluble film 112 dissolves and the powdery water-absorbent synthetic resin absorbs water to swell into gels so that the deodorant and perfume are entrapped therein. The polyacrylic acid incorporated in this pack 110 is capable of absorbing 200 cc to 300 cc of water per gram and does not easily release the water once absorbed. Moreover, since the polyacrylic acid has a moisture-releasing property, it allows the deodorant or the like, which cannot emanate as such, to be released into the atmospheric air.

Figure 4:
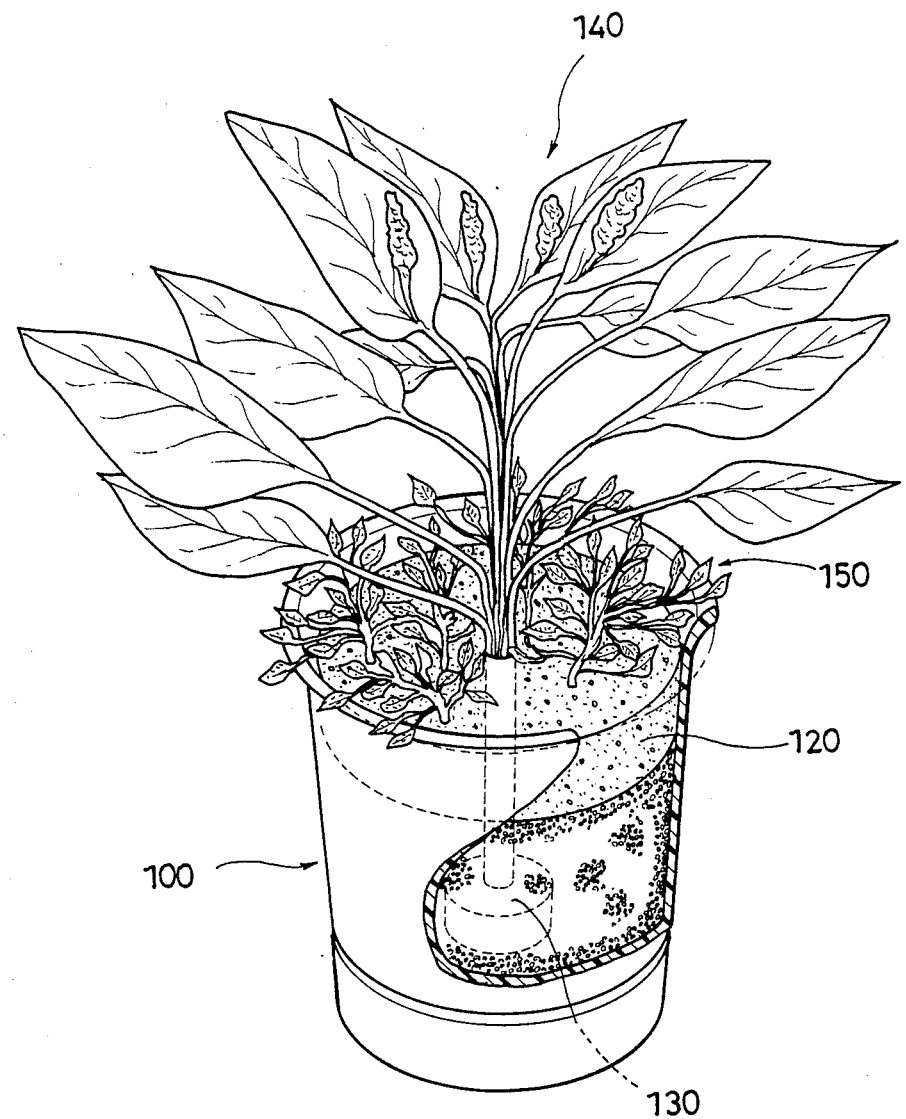

FIG. 4 is a partially exploded generally perspective view showing the artificial potted flower after addition of water. When an appropriate quantity of water is poured from the top of the cover plate 120 onto the artificial potted flower, the water passes through the cover plate 120 made of polyurethane foam to reach the packs 110 within the vessel. The soluble synthetic resin 112 forming the pack is dissolved by this water and swells in the form of gels as illustrated, filling the free space within the vessel. The perfume and deodorant entrapped in the gels of water-absorbent synthetic resin upon absorption of water are then emanated through the air-permeable cover plate 120 into the surrounding atmospheric air, thereby assuring the desired deodorant and scenting effect over a protracted time period.

Furthermore, because the stalk portion 141 of the artificial flower 140 is supported by both the cover plate 120 and support means 130, the planted artificial flower is kept securely in position. In addition, since the weight of the vessel 100 is increased on addition of water to the vessel, the whole artificial flower-pot assembly is maintained in a highly stable position. Should the vessel fall on its side or upside down, the polyacrylic acid in the vessel would not readily release the absorbed water so that there is no fear of outflow of water.

Figure 5:
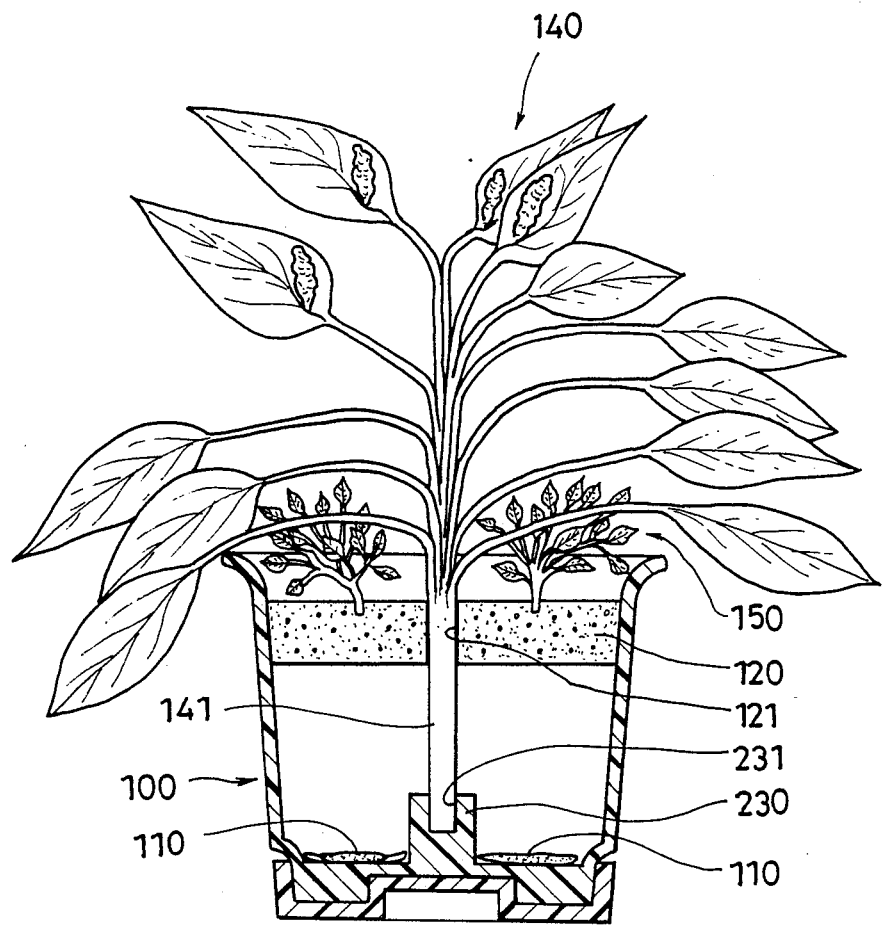
Figure 6:
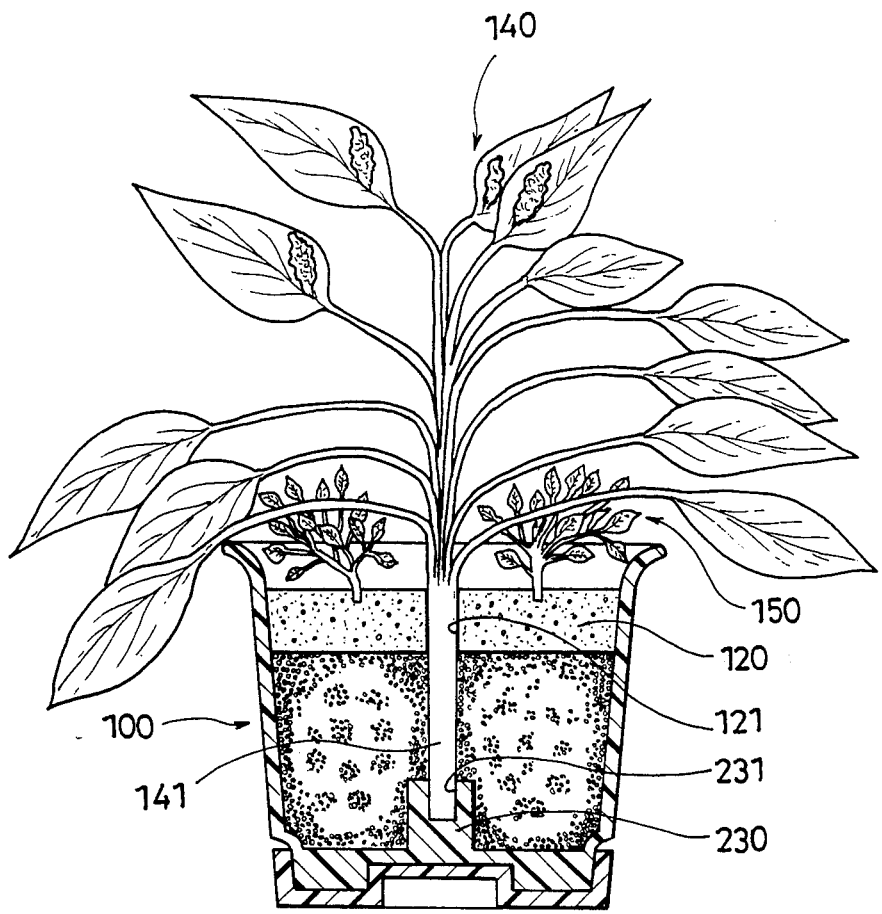

FIGS. 5 and 6 show another embodiment of this invention. FIG. 5 is a cross-section view and FIG. 6 is a cross-section view after addition of water. In this embodiment, the support means of polystyrene foam secured to the inner bottom of the vessel is replaced with a support means 230 integrally formed with the vessel and this integral support means 230 is provided with a bearing hole 231 for supporting the bottom end of the stalk portion of the artificial flower. In this embodiment, it is not necessary to fabricate an independent support and attach it to the vessel so that the manufacture of the artificial potted flower is faciliated.

It should be understood that the materials, shapes and sizes of the artificial flower and vessel, the kinds and amounts of the powdery perfume, powdery deodorant, powdery water-absorbent synthetic resin and soluble film encasing them, which constitute the artificial potted flower of this invention, are not limited to those mentioned in the foregoing description of preferred embodiments.

What is claimed is:

1. An artificial potted flower comprising an artificial flower, a vessel in which the artificial flower is planted, a pack consisting of a casing of water soluble film and, contained therein, a mixture of a powdery deodorant and a powdery water-absorbent synthetic resin, said pack being disposed within said vessel, a cover plate of porous synthetic resin fitted in a top portion of said vessel, and a support means for supporting said artificial flower said support means being disposed in the bottom portion of said vessel in such a manner that a stalk portion of said artificial flower may be passed through said cover plate and secured rigidly to said support means.

2. An artificial potted flower comprising an artificial flower, a vessel in which the artificial flower is planted, a pack consisting of a casing of water soluble film and, contained therein, a mixture of a powdery perfume and a powdery water-absorbent synthetic resin, said pack being disposed within said vessel, a cover plate of porous synthetic resin fitted in a top portion of said vessel, and a support means for supporting said artificial flower said support means being disposed in the bottom portion of said vessel in such a manner that a stalk portion of said artificial flower may be passed through said cover plate and secured rigidly to said support means.

3. An artificial potted flower comprising an artificial flower, a vessel in which the artificial flower is planted, a pack consisting of a casing of water soluble film and, contained therein, a mixture of a powdery deodorant, a powdery perfume and a powdery water-absorbent synthetic resin, said pack being disposed within said vessel, a cover plate of porous synthetic resin fitted in a top portion of said vessel, and a support means for supporting said artificial flower said support means being disposed in the bottom portion of said vessel in such a manner that a stalk portion of said artificial flower may be passed through said cover plate and secured rigidly to said support means.

* * * * *